US012667725B2

(12) United States Patent
Alfsmann et al.

(10) Patent No.: US 12,667,725 B2
(45) Date of Patent: Jun. 30, 2026

(54) SYSTEMS AND METHODS FOR TRAINING A MACHINE LEARNING MODEL FOR USE BY A PROCESSING UNIT IN A COCHLEAR IMPLANT SYSTEM

(71) Applicant: Advanced Bionics AG, Staefa (CH)

(72) Inventors: Daniel J. Alfsmann, Valencia, CA (US); Raphael S. Koning, Wedemark (DE); Joachim Thiemann, Hannover (DE)

(73) Assignee: Advanced Bionics AG, Staefa (CH)

( * ) Notice: Subject to any disclaimer, the term of this patent is extended or adjusted under 35 U.S.C. 154(b) by 1162 days.

(21) Appl. No.: 17/620,040

(22) PCT Filed: Jul. 10, 2020

(86) PCT No.: PCT/US2020/041702
§ 371 (c)(1),
(2) Date: Dec. 16, 2021

(87) PCT Pub. No.: WO2021/007558
PCT Pub. Date: Jan. 14, 2021

(65) Prior Publication Data
US 2022/0249844 A1     Aug. 11, 2022

Related U.S. Application Data

(60) Provisional application No. 62/873,114, filed on Jul. 11, 2019.

(51) Int. Cl.
*A61N 1/36*     (2006.01)
*G06N 3/08*     (2023.01)
*G16H 40/63*     (2018.01)

(52) U.S. Cl.
CPC ........... *A61N 1/36039* (2017.08); *G06N 3/08* (2013.01); *G16H 40/63* (2018.01)

(58) Field of Classification Search
CPC ....... A61N 1/36039; G16H 40/63; G06N 3/08
See application file for complete search history.

(56) References Cited

U.S. PATENT DOCUMENTS 5,626,629 A * 5/1997 Faltys ................ A61N 1/36038
607/57
2011/0286618 A1* 11/2011 Vandali .............. A61N 1/36038
381/320

(Continued)

OTHER PUBLICATIONS

"International Search Report and Written Opinion received in International Application No. PCT/US20/41702."

(Continued)

Primary Examiner — William J Levicky
Assistant Examiner — Jessandra F Hough
(74) Attorney, Agent, or Firm — ALG Intellectual Property, LLC

(57)     ABSTRACT

An exemplary system is configured to maintain data representative a machine learning model for use in a cochlear implant system and train the machine learning model. The training may include applying audio content as a training input to the machine learning model, the machine learning model configured to apply a machine learning heuristic to the audio content to output an electrical signal representative of the audio content; applying the electrical signal to a brain processing model, the brain processing model configured to output synthesized audio content representative of the electrical signal; generating an error metric representative of a difference between the audio content and the synthesized audio content; and feeding back the error metric into the machine learning model, the machine learning model configured to use the error metric to adjust the machine learning heuristic applied to the audio content.

9 Claims, 15 Drawing Sheets

(56)                    References Cited

U.S. PATENT DOCUMENTS

| | | |
|---|---|---|
| 2017/0080226 A1* | 3/2017 | Akhoun ............. A61N 1/37241 |
| 2019/0132687 A1 | 5/2019 | Santos et al. |
| 2019/0182606 A1 | 6/2019 | Petersen |
| 2020/0314568 A1* | 10/2020 | El Guindi ............ H04R 25/407 |

OTHER PUBLICATIONS

Aubreville, et al., "Deep Neural Networks for Noise Reduction under Hearing Aid Side Conditions," IHCON 2018, Lake Tahoe, CA.
Goehring, et al., "Speech enhancement based on neural networks improves speech intelligibility in noise for cochlear implant users," Hearing Research 344, pp. 183-194, 2017.
Tenorio, et al., "Using Neural Networks to Improve Cochlear Implant Speech Perception," Proc. Neural Information Processing Systems 1 (NIPS 1987), 1988: Description of NN for CI stimulation channel selection.

\* cited by examiner

100
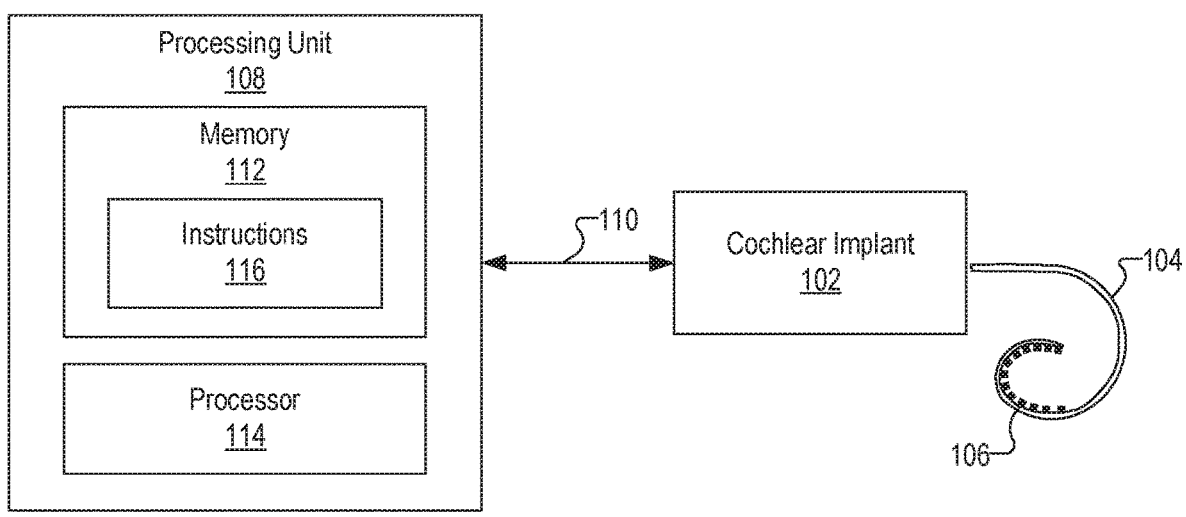
Fig. 1

200

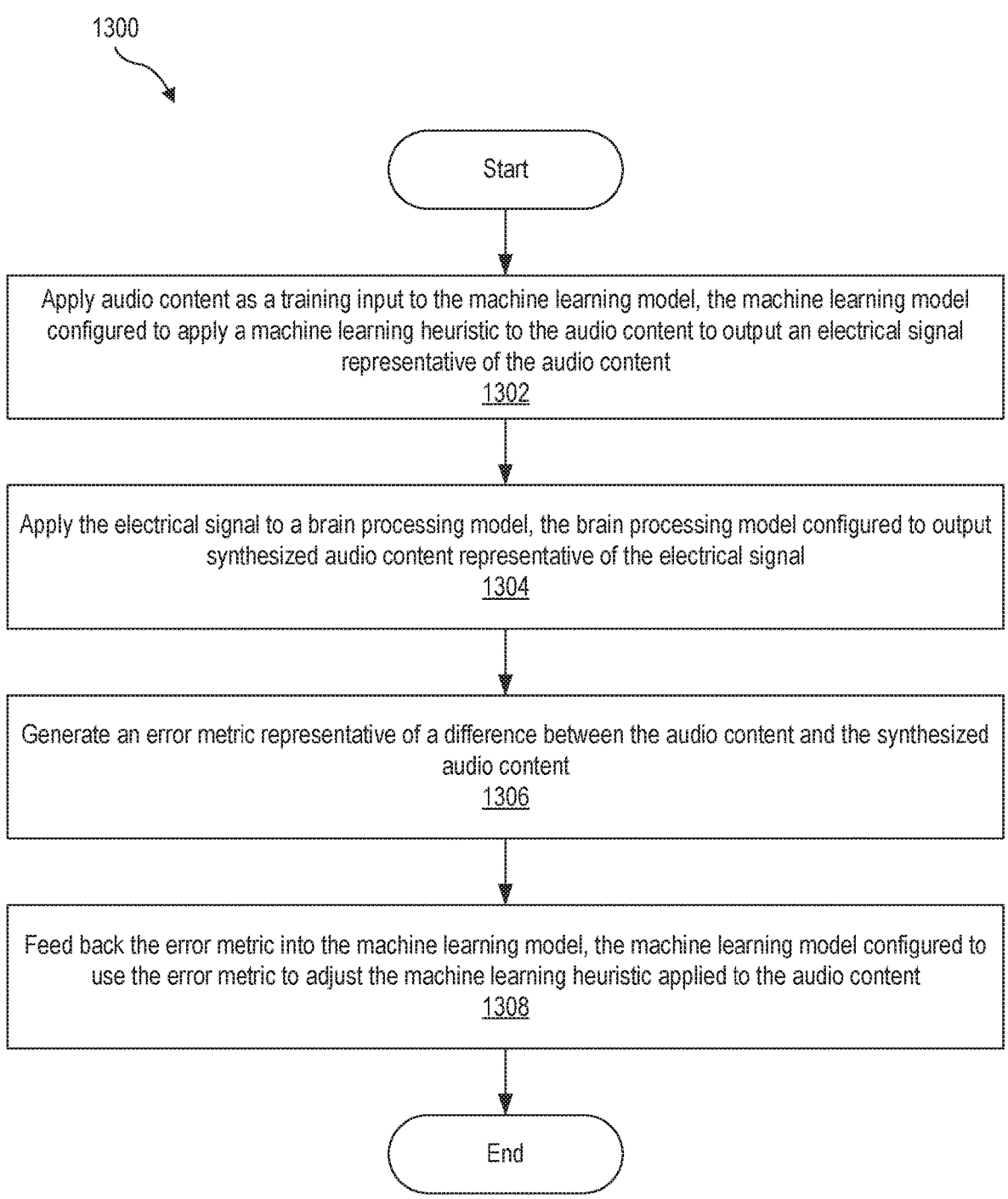

1300

Start

Apply audio content as a training input to the machine learning model, the machine learning model configured to apply a machine learning heuristic to the audio content to output an electrical signal representative of the audio content
1302

Apply the electrical signal to a brain processing model, the brain processing model configured to output synthesized audio content representative of the electrical signal
1304

Generate an error metric representative of a difference between the audio content and the synthesized audio content
1306

Feed back the error metric into the machine learning model, the machine learning model configured to use the error metric to adjust the machine learning heuristic applied to the audio content
1308

End

Fig. 13

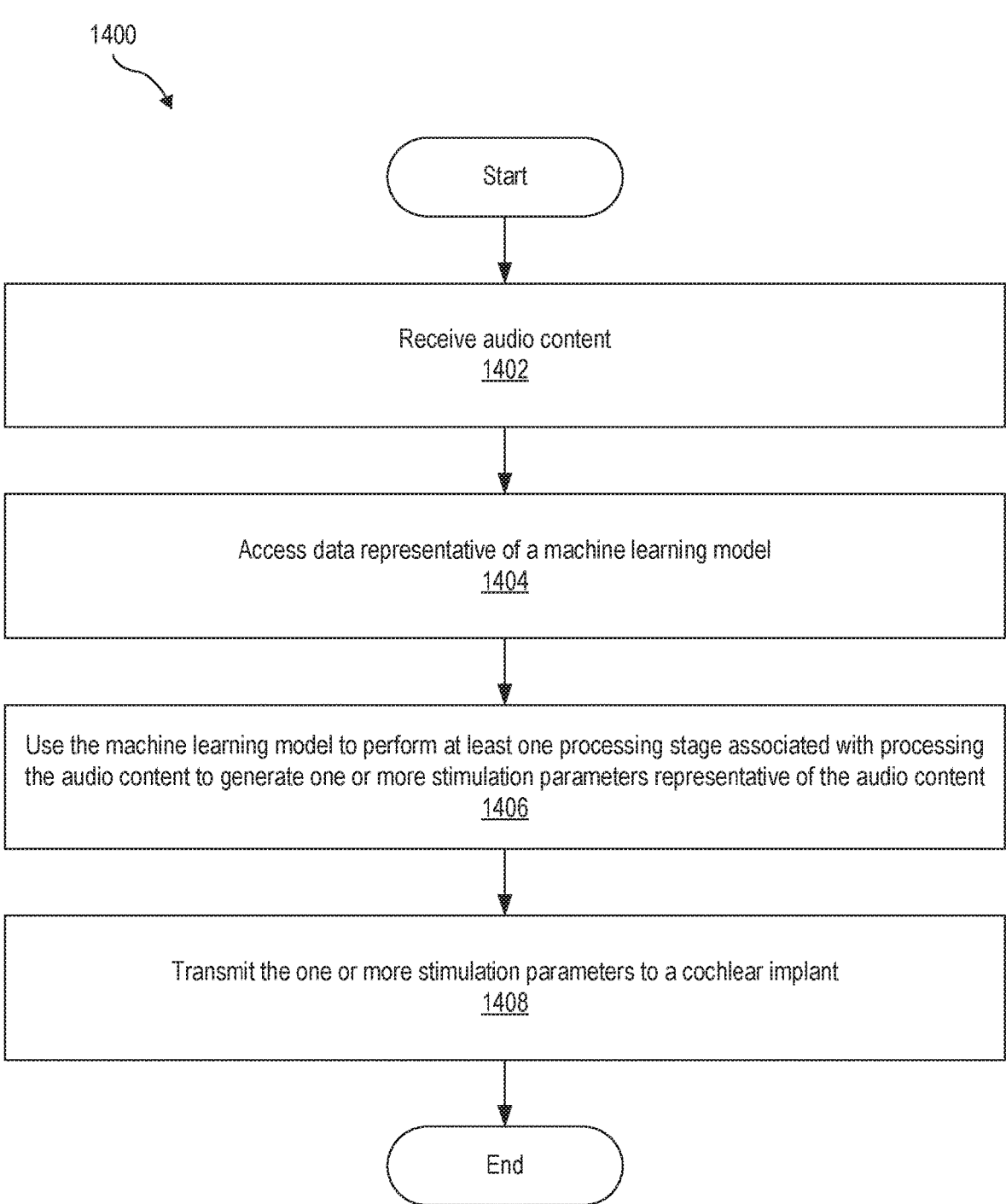

1400

Start

Receive audio content
1402

Access data representative of a machine learning model
1404

Use the machine learning model to perform at least one processing stage associated with processing the audio content to generate one or more stimulation parameters representative of the audio content
1406

Transmit the one or more stimulation parameters to a cochlear implant
1408

End

Fig. 14

SYSTEMS AND METHODS FOR TRAINING A MACHINE LEARNING MODEL FOR USE BY A PROCESSING UNIT IN A COCHLEAR IMPLANT SYSTEM

RELATED APPLICATIONS

The present application claims priority to U.S. Provisional Patent Application No. 62/873,114, filed Jul. 11, 2019, the contents of which are hereby incorporated by reference in their entirety.

BACKGROUND INFORMATION

Cochlear implant systems conventionally include a processing unit (e.g., a behind-the-ear sound processor) and a cochlear implant configured to be implanted within a hearing impaired recipient. The processing unit is configured to process audio content (e.g., speech or other sound) presented to the recipient in accordance with a sound processing strategy to generate stimulation parameters. The processing unit is further configured to transmit the stimulation parameters to the cochlear implant, which uses the stimulation parameters to generate and apply electrical stimulation representative of the audio content to the recipient. In this way, the recipient may perceive the audio content.

Cochlear implant system performance (e.g., in terms of quality of audio perception by a recipient, power consumption, etc.) in large part depends on the particular sound processing strategy used by the processing unit to process the audio content presented to the recipient. Unfortunately, it is often difficult to optimize sound processing strategies, as they depend on a combination of a large number of variables and are challenging to objectively assess. Indeed, conventional approaches to improving sound processing strategies used by processing units often provide only non-significant performance gains, and sometimes inadvertently decrease performance in some use cases and/or for a subset of the cochlear implant recipient population.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 1 illustrates an exemplary cochlear implant system.

FIGS. 12-14 illustrate exemplary methods.

DETAILED DESCRIPTION

Figure 2:
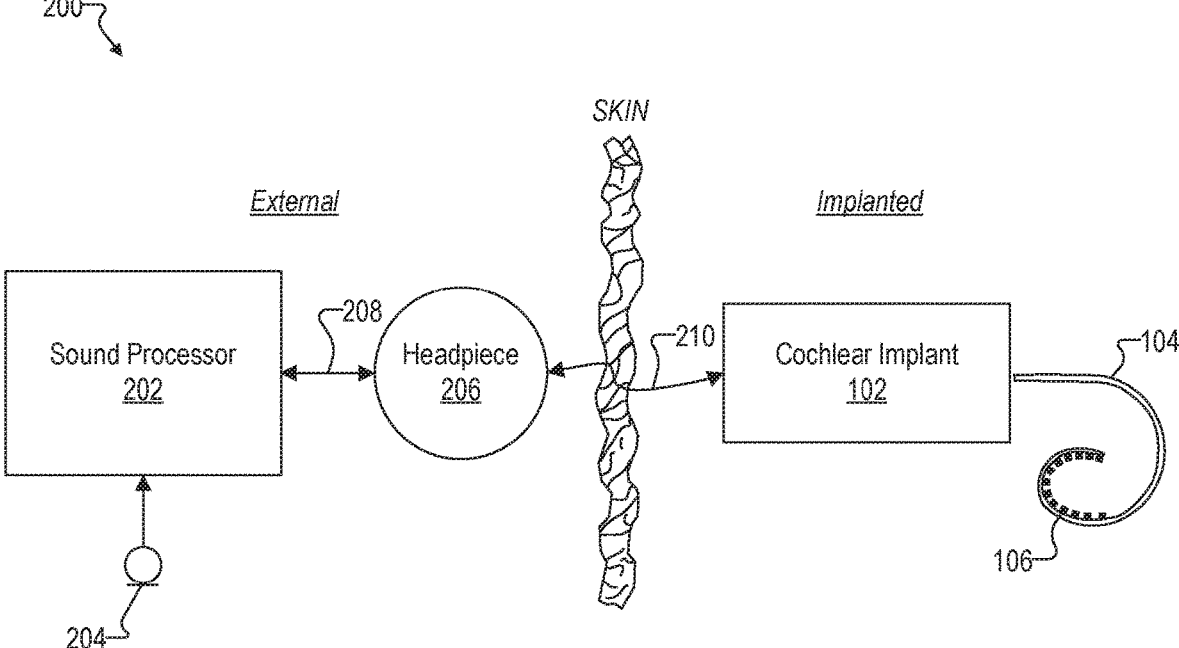
FIG. 2 shows an exemplary configuration of the cochlear implant system of FIG. 1.

Systems and methods for training a machine learning model for use in a cochlear implant system are described herein. For example, as described herein, a model management system may maintain data representative a machine learning model for use in a cochlear implant system and train the machine learning model by 1) applying audio content as a training input to the machine learning model, the machine learning model configured to apply a machine learning heuristic to the audio content to output an electrical signal representative of the audio content, 2) applying the electrical signal to a brain processing model, the brain processing model configured to output synthesized audio content representative of the electrical signal, 3) generating an error metric representative of a difference between the audio content and the synthesized audio content, and 4) feeding back the error metric into the machine learning model, the machine learning model configured to use the error metric to adjust the machine learning heuristic applied to the audio content.

In some examples, data representative of the trained machine learning model may be transmitted to or otherwise provided for use by a processing unit in a cochlear implant system. The processing unit may be configured to use the machine learning model to perform one or more processing stages associated with processing audio content received by the processing unit to generate one or more stimulation parameters representative of the audio content.

The machine learning model based systems and methods described herein may provide many benefits and advantages compared to conventional sound processing techniques. For example, the systems and methods described herein may allow sound processing strategies used by processing units in cochlear implant systems to be optimized globally for optimum performance, leveraging vast amounts of training data available to manufacturers or other entities associated with cochlear implant systems. Moreover, the systems and methods described herein may simplify or even eliminate the need for some types of fitting procedures, which may save clinicians and recipients time and resources. Moreover, the systems and methods described herein may substantially reduce the amount of power required by a processing unit to process audio content, thereby preserving battery life and enabling the manufacture of smaller devices. These and other benefits and advantages of the systems and methods described herein will be made apparent herein.

FIG. 1 illustrates an exemplary cochlear implant system 100 configured to be used by a recipient. As shown, cochlear implant system 100 includes a cochlear implant 102, an electrode lead 104 physically coupled to cochlear implant 102 and having an array of electrodes 106, and a processing unit 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and electrode leads for each ear of the recipient. In the bilateral configuration, processing unit 108 may be implemented by a single processing unit configured to interface with both cochlear implants or by two separate processing units each configured to interface with a different one of the cochlear implants.

Cochlear implant 102 may be implemented by any suitable type of implantable stimulator. For example, cochlear implant 102 may be implemented by an implantable cochlear stimulator. Additionally or alternatively, cochlear implant 102 may be implemented by a brainstem implant and/or any other type of device that may be implanted within the recipient and configured to apply electrical stimulation to one or more stimulation sites located along an auditory pathway of the recipient.

In some examples, cochlear implant 102 may be configured to generate electrical stimulation representative of an audio signal (also referred to herein as audio content) processed by processing unit 108 in accordance with one or more stimulation parameters transmitted to cochlear implant 102 by processing unit 108. Cochlear implant 102 may be further configured to apply the electrical stimulation to one or more stimulation sites (e.g., one or more intracochlear locations) within the recipient by way of one or more electrodes 106 on electrode lead 104. In some examples, cochlear implant 102 may include a plurality of independent current sources each associated with a channel defined by one or more of electrodes 106. In this manner, different stimulation current levels may be applied to multiple stimulation sites simultaneously by way of multiple electrodes 106.

Cochlear implant 102 may additionally or alternatively be configured to generate, store, and/or transmit data. For example, cochlear implant may use one or more electrodes 106 to record one or more signals (e.g., one or more voltages, impedances, evoked responses within the recipient, and/or other measurements) and transmit, by way of communication link 110, data representative of the one or more signals to processing unit 108. In some examples, this data is referred to as back telemetry data.

Electrode lead 104 may be implemented in any suitable manner. For example, a distal portion of electrode lead 104 may be pre-curved such that electrode lead 104 conforms with the helical shape of the cochlea after being implanted. Electrode lead 104 may alternatively be naturally straight or of any other suitable configuration.

In some examples, electrode lead 104 includes a plurality of wires (e.g., within an outer sheath) that conductively couple electrodes 106 to one or more current sources within cochlear implant 102. For example, if there are n electrodes 106 on electrode lead 104 and n current sources within cochlear implant 102, there may be n separate wires within electrode lead 104 that are configured to conductively connect each electrode 106 to a different one of the n current sources. Exemplary values for n are 8, 12, 16, or any other suitable number.

Electrodes 106 are located on at least a distal portion of electrode lead 104. In this configuration, after the distal portion of electrode lead 104 is inserted into the cochlea, electrical stimulation may be applied by way of one or more of electrodes 106 to one or more intracochlear locations. One or more other electrodes (e.g., including a ground electrode, not explicitly shown) may also be disposed on other parts of electrode lead 104 (e.g., on a proximal portion of electrode lead 104) to, for example, provide a current return path for stimulation current applied by electrodes 106 and to remain external to the cochlea after the distal portion of electrode lead 104 is inserted into the cochlea. Additionally or alternatively, a housing of cochlear implant 102 may serve as a ground electrode for stimulation current applied by electrodes 106.

Processing unit 108 may be configured to interface with (e.g., control and/or receive data from) cochlear implant 102. For example, processing unit 108 may transmit commands (e.g., stimulation parameters and/or other types of operating parameters in the form of data words included in a forward telemetry sequence) to cochlear implant 102 by way of communication link 110. Processing unit 108 may additionally or alternatively provide operating power to cochlear implant 102 by transmitting one or more power signals to cochlear implant 102 by way of communication link 110. Processing unit 108 may additionally or alternatively receive data from cochlear implant 102 by way of communication link 110. Communication link 110 may be implemented by any suitable number of wired and/or wireless bidirectional and/or unidirectional links.

As shown, processing unit 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferro-electric random-access memory ("RAM"), and an optical disc. Exemplary volatile storage media include, but are not limited to, RAM (e.g., dynamic RAM).

Memory 112 may maintain (e.g., store) executable data used by processor 114 to perform one or more of the operations described herein as being performed by processing unit 108. For example, memory 112 may store instructions 116 that may be executed by processor 114 to perform any of the audio content processing and cochlear implant control operations described herein. Instructions 116 may be implemented by any suitable application, program (e.g., sound processing program), software, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102.

To illustrate, processor 114 may be configured to control an operation of cochlear implant 102. For example, processor 114 may receive an audio signal (e.g., by way of a microphone communicatively coupled to processing unit 108, a wireless interface (e.g., a Bluetooth interface), and/or a wired interface (e.g., an auxiliary input port)). Processor 114 may process the audio signal in accordance with a sound processing strategy (e.g., a sound processing program stored in memory 112) to generate appropriate stimulation parameters. Processor 114 may then transmit the stimulation parameters to cochlear implant 102 to direct cochlear implant 102 to apply electrical stimulation representative of the audio signal to the recipient.

In some implementations, processor 114 may also be configured to apply acoustic stimulation to the recipient. For example, a receiver (also referred to as a loudspeaker) may be optionally coupled to processing unit 108. In this configuration, processor 114 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 114 is configured to both deliver acoustic stimulation to the recipient and direct cochlear implant 102 to apply electrical stimulation to the recipient, cochlear implant system 100 may be referred to as a bimodal hearing system and/or any other suitable term.

Processor 114 may be additionally or alternatively configured to receive and process data generated by cochlear implant 102. For example, processor 114 may receive data representative of a signal recorded by cochlear implant 102 using one or more electrodes 106 and, based on the data, adjust one or more operating parameters of processing unit 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by processing unit 108 and/or any implementation thereof may be understood to be performed by processor 114 based on instructions 116 stored in memory 112.

Processing unit 108 may be implemented by one or more devices configured to interface with cochlear implant 102. To illustrate, FIG. 2 shows an exemplary configuration 200 of cochlear implant system 100 in which processing unit 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear ("BTE") unit configured to be worn behind and/or on top of an ear of the recipient. Additionally or alternatively, sound processor 202 may be implemented by an off-the-ear unit (also referred to as a body worn device) configured to be worn or carried by the recipient away from the ear. Additionally or alternatively, at least a portion of sound processor 202 is implemented by circuitry within headpiece 206.

Microphone 204 is configured to detect one or more audio signals (e.g., that include speech and/or any other type of sound) in an environment of the recipient. Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone as may serve a particular implementation.

Headpiece 206 may be selectively and communicatively coupled to sound processor 202 by way of a communication link 208 (e.g., a cable or any other suitable wired or wireless communication link), which may be implemented in any suitable manner. Headpiece 206 may include an external antenna (e.g., a coil and/or one or more wireless communication components) configured to facilitate selective wireless coupling of sound processor 202 to cochlear implant 102. Headpiece 206 may additionally or alternatively be used to selectively and wirelessly couple any other external device to cochlear implant 102. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise connected to cochlear implant 102. In this manner, stimulation parameters and/or power signals may be wirelessly and transcutaneously transmitted between sound processor 202 and cochlear implant 102 by way of a wireless communication link 210.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply electrical stimulation representative of the audio signal to the recipient.

In an alternative configuration, sound processor 202 may be implanted within the recipient instead of being located external to the recipient. In this alternative configuration, which may be referred to as a fully implantable configuration of cochlear implant system 100, sound processor 202 and cochlear implant 102 may be combined into a single device or implemented as separate devices configured to communicate one with another by way of a wired and/or wireless communication link. In a fully implantable implementation of cochlear implant system 100, headpiece 206 may not be included and microphone 204 may be implemented by one or more microphones implanted within the recipient, located within an ear canal of the recipient, and/or external to the recipient.

Figure 3:
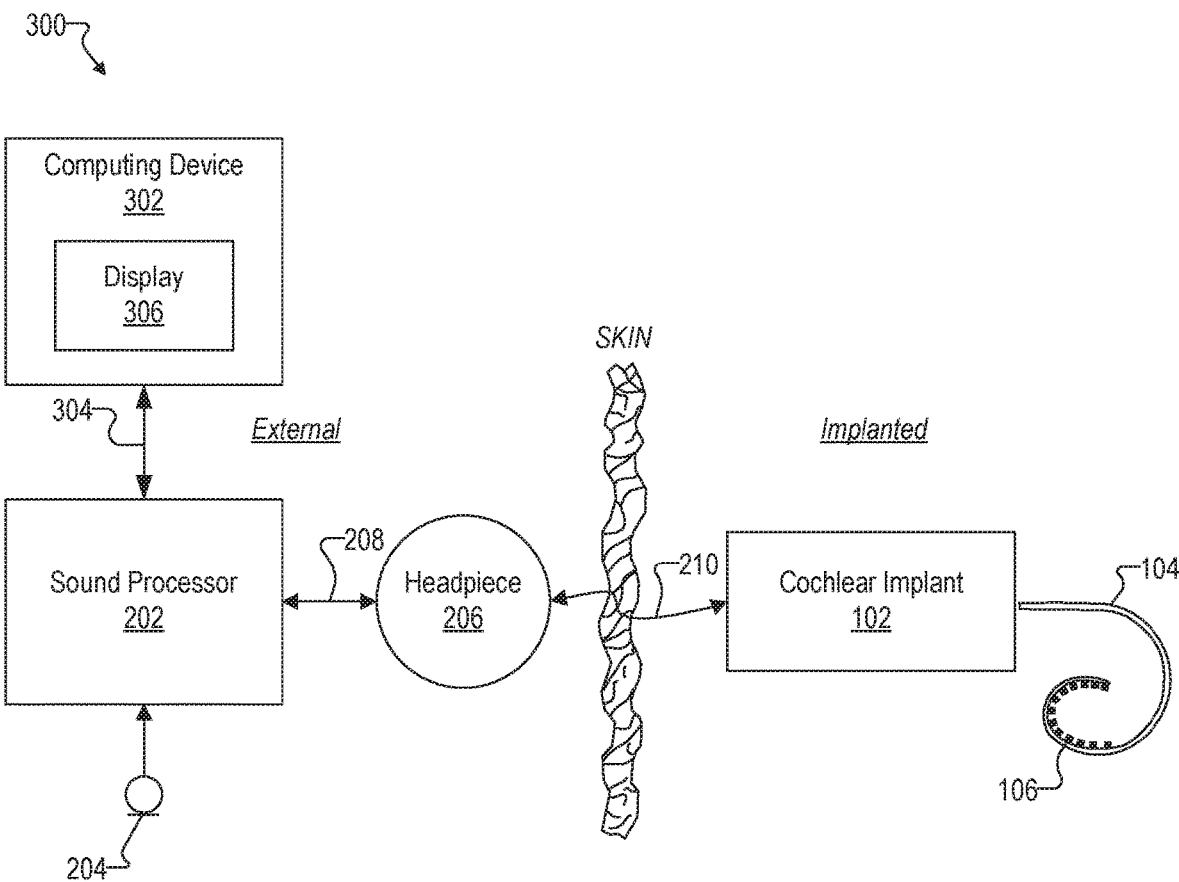
FIG. 3 shows another exemplary configuration of the cochlear implant system of FIG. 1.

FIG. 3 shows an exemplary configuration 300 of cochlear implant system 100 in which processing unit 108 is implemented by a combination of sound processor 202 and a computing device 302 configured to communicatively couple to sound processor 202 by way of a communication link 304, which may be implemented by any suitable wired or wireless communication link.

Computing device 302 may be implemented by any suitable combination of hardware and software. To illustrate, computing device 302 may be implemented by a mobile device (e.g., a mobile phone, a laptop, a tablet computer, etc.), a desktop computer, and/or any other suitable computing device as may serve a particular implementation. As an example, computing device 302 may be implemented by a mobile device configured to execute an application (e.g., a "mobile app") that may be used by a user (e.g., the recipient, a clinician, and/or any other user) to control one or more settings of sound processor 202 and/or cochlear implant 102 and/or perform one or more operations (e.g., diagnostic operations) with respect to data generated by sound processor 202 and/or cochlear implant 102.

In some examples, computing device 302 may be configured to control an operation of cochlear implant 102 by transmitting one or more commands to cochlear implant 102 by way of sound processor 202. Likewise, computing device 302 may be configured to receive data generated by cochlear implant 102 by way of sound processor 202. Alternatively, computing device 302 may interface with (e.g., control and/or receive data from) cochlear implant 102 directly by way of a wireless communication link between computing device 302 and cochlear implant 102. In some implementations in which computing device 302 interfaces directly with cochlear implant 102, sound processor 202 may or may not be included in cochlear implant system 100.

Computing device 302 is shown as having an integrated display 306. Display 306 may be implemented by a display screen, for example, and may be configured to display content generated by computing device 302. Additionally or alternatively, computing device 302 may be communicatively coupled to an external display device (not shown) configured to display the content generated by computing device 302.

In some examples, computing device 302 represents a fitting device configured to be selectively used (e.g., by a clinician) to fit sound processor 202 and/or cochlear implant 102 to the recipient. In these examples, computing device 302 may be configured to execute a fitting program configured to set one or more operating parameters of sound processor 202 and/or cochlear implant 102 to values that are optimized for the recipient. As such, in these examples, computing device 302 may not be considered to be part of cochlear implant system 100. Instead, computing device 302 may be considered to be separate from cochlear implant system 100 such that computing device 302 may be selectively coupled to cochlear implant system 100 when it is desired to fit sound processor 202 and/or cochlear implant 102 to the recipient.

Figure 4:
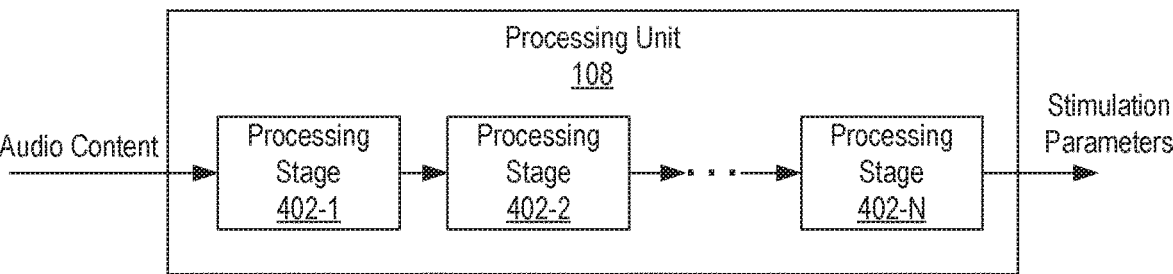
FIG. 4 illustrates an exemplary sound processing strategy employed by a processing unit.

FIG. 4 illustrates an exemplary sound processing strategy employed by processing unit 108. As shown, processing unit 108 may process incoming audio content in a plurality of processing stages 402 (e.g., processing stage 402-1 through processing stage 402-N). Processing stages 402 may be performed in series, as shown in FIG. 4. Alternatively, two or more processing stages 402 may be performed in parallel.

Each processing stage 402 may represent one or more processing operations performed with respect to audio content received by processing unit 108. For example, an exemplary processing stage may include a pre-processing stage in which the audio content is filtered and/or gain corrected. Another exemplary processing stage may divide an audio signal into a plurality of analysis channels each corresponding to a different frequency band and perform channel-specific operations in each analysis channel. Another exemplary processing stage may include an electrode mapping stage in which patient-specific parameters (e.g., most comfortable stimulation levels (M levels), threshold levels (T levels), current steering parameters, electrode enabling and disabling parameters, and electrode mapping operations are performed. Another exemplary processing stage may include an N-of-M channel selection stage in which N of M total stimulation channels are selected for use by the cochlear implant to represent the audio content to the recipient. Another exemplary processing stage may include a noise reduction stage in which noise within the audio content is reduced or eliminated. Additional or alternative operations may be performed in these and/or other processing stages 402 as may serve a particular implementation.

As described herein, processing unit 108 may be configured to use a machine learning model to perform one or more of the processing stages 402. To that end, a model management system may maintain, train, and provide processing unit 108 with access to a machine learning mode.

Figure 5:
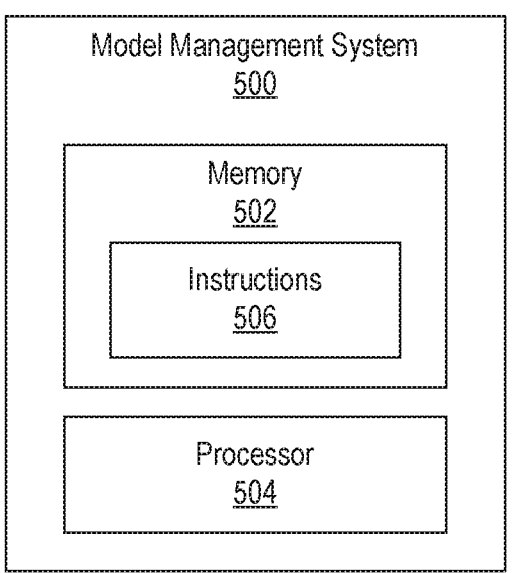
FIG. 5 shows an exemplary model management system.

FIG. 5 shows an exemplary model management system 500 ("system 500"). System 500 may be implemented by one or more computing devices (e.g., servers) not included in (e.g., remote from) any of the cochlear implant systems described herein. For example, system 500 may be implemented by one or more computing devices maintained and/or otherwise associated with a manufacturer of cochlear implant systems, a provider of cochlear implant systems, and/or any other entity as may serve a particular implementation.

As shown, system 500 includes a memory 502 and a processor 504 configured to be selectively and communicatively coupled to one another. In some examples, memory 502 and processor 504 may be distributed between multiple devices and/or multiple locations as may serve a particular implementation.

Memory 502 may be implemented by any suitable non-transitory computer-readable medium and/or non-transitory processor-readable medium, such as any combination of non-volatile storage media and/or volatile storage media as described herein.

Memory 502 may maintain (e.g., store) executable data used by processor 504 to perform one or more of the operations described herein as being performed by system 500. For example, memory 502 may store instructions 506 that may be executed by processor 504 to perform any of the machine learning model maintenance and training operations described herein. Instructions 506 may be implemented by any suitable application, program, software, code, and/or other executable data instance. Memory 502 may also maintain any data received, generated, managed, used, and/or transmitted by processor 504.

Processor 504 may be configured to perform (e.g., execute instructions 506 stored in memory 502 to perform) various operations with respect to maintaining and training a machine learning model for use in one or more cochlear implant systems. In the description provided herein, any references to operations performed by system 500 and/or any implementation thereof may be understood to be performed by processor 504 based on instructions 506 stored in memory 502.

Figure 6:
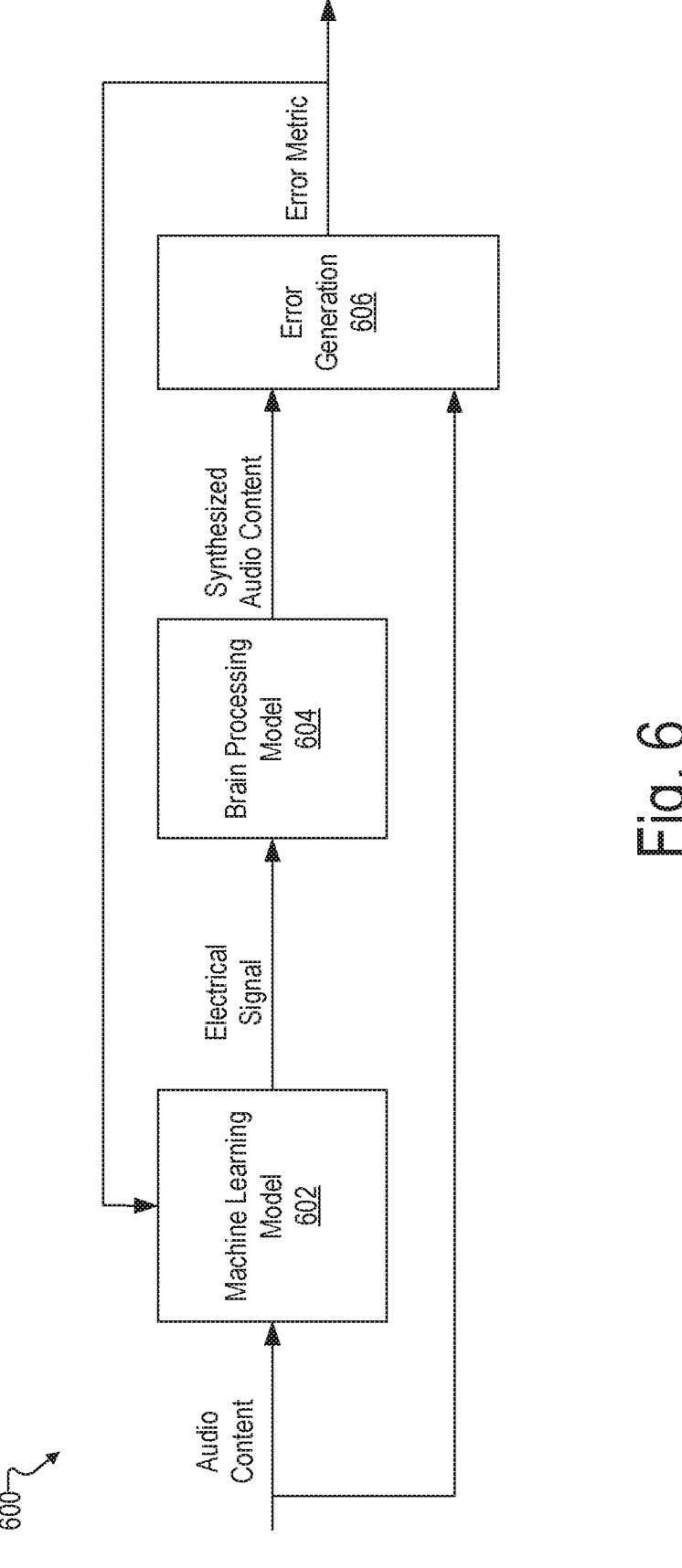
FIG. 6 shows an exemplary implementation of operations performed by a model management system to maintain and train a machine learning model.

FIG. 6 shows an exemplary implementation 600 of operations performed by system 500 to maintain and train a machine learning model. The operations described in connection with FIG. 6 are merely illustrative of the many different ways in which system 500 may maintain and train a machine learning model.

As shown, system 500 may maintain data representative of a machine learning model 602 for use in a cochlear implant system. Machine learning model 602 may be configured to perform any suitable machine learning heuristic (also referred to as artificial intelligence heuristic) to input data, which may be in either the time or frequency domains. Machine learning model 602 may accordingly be supervised and/or unsupervised as may serve a particular implementation and may be configured to implement one or more decision tree learning algorithms, association rule learning algorithms, artificial neural network learning algorithms, deep learning algorithms, bitmap algorithms, and/or any other suitable data analysis technique as may serve a particular implementation.

In some examples, machine learning model 602 is implemented by one or more neural networks, such as one or more deep convolutional neural networks (CNN) using internal memories of its respective kernels (filters), recurrent neural networks (RNN), and/or long/short term memory neural networks (LSTM). Machine learning model 602 may be multi-layer. For example, machine learning model 602 may be implemented by a neural network that includes an input layer, one or more hidden layers, and an output layer.

System 500 may train machine learning model 602 in any suitable manner. For example, system 500 may train machine learning model 602 using an autoencoder scheme in connection with a brain processing model (e.g., a vocoder).

To illustrate, FIG. 6 shows that system 600 may apply audio content (also referred to herein as "training audio content") as a training input to machine learning model 602. The audio content may include any suitable type of audio content as may serve a particular implementation. For example, the audio content may include pre-recorded or live speech content, music content, noisy audio content, clean audio content without noise, etc. The audio content may be applied to machine learning model 602 in the form of a time domain signal or in the form of a frequency domain signal.

Any number of audio content instances (e.g., different audio samples) may be used to train machine learning model 602. Each audio content instance may be of any suitable duration. Moreover, because no human operation and/or interpretation is needed to train machine learning model 602, system 600 may apply as much audio content as may be needed (e.g., hours or even days worth of audio content) to effectively train machine learning model 602. Since labeled data may not be needed, machine learning model 602 may be trained with a large number of audio samples that can be found from various sources.

In some examples, system 500 is configured to pre-process the audio content before the audio content is applied as the training input to machine learning model 602. Such pre-processing may include filtering, gain correcting, and/or any other pre-processing operation that may be typically performed by processing unit 108 on audio content prior to the audio content being processed by a digital signal processor (DSP). Alternatively, such pre-processing may not be performed such that raw audio content is applied as the training input to machine learning model 602.

Machine learning model 602 may be configured to apply a machine learning heuristic to the audio content to output an electrical signal representative of the audio content. The machine learning heuristic may be any of the machine learning heuristics described herein, such as one or more neural network processing heuristics.

As mentioned, machine learning model 602 may be configured to output an electrical signal representative of the audio content. The electrical signal may include one or more electrical stimulation pulses that a cochlear implant would apply to a recipient of the cochlear implant system to represent the audio content to the recipient. In some example, machine learning model 602 may generate the electrical signal by generating one or more stimulation parameters that define the electrical signal. For example, machine learning model 602 may generate data representative of an amplitude, pulse width, frequency, duration, electrode mapping scheme, etc. that together define various properties of the electrical signal.

As shown, the electrical signal output by machine learning model 602 may be applied to a brain processing model 604. Brain processing model 604 may be configured to output synthesized audio content representative of the electrical signal. This may be performed in any suitable manner.

Brain processing model 604 may be implemented by any suitable model that is configured to model how a brain of a cochlear implant recipient would process and/or perceive an electrical signal representative of audio content. For example, brain processing model 604 may be implemented by a vocoder configured to process the electrical signal output by machine learning model 602 in accordance with one or more audio synthesis heuristics to output synthesized audio content representative of the electrical signal.

System 500 may be configured to generate an error metric representative of a difference between the audio content and the synthesized audio content. For example, as shown in FIG. 6, the synthesized audio content and the original audio content may be input into an error generation function 606. Error generation function 606 may be configured to compare the audio content and the synthesized audio content in any suitable manner to output an error metric representative of a difference between the audio content and the synthesized audio content.

For example, error generation function 606 may implement a cost/error function. The cost function may, for example, consist of the total energy of a difference signal or spectrum with respect to the audio content and the synthesized audio content, a maximum peak of the difference signal or spectrum of the difference signal, and/or any other norm on the difference signal or spectrum. The difference signal may in some examples be created such that the synthesized audio content is transformed before taking the difference, e.g., by frequency shifting according to an expected frequency mismatch by the electrode location within the cochlear, modelled by brain processing model 604.

In some examples, error generation function 606 may generate the error metric based on a model of the perceptible difference between the audio content and the synthesized audio content, for example by using a psychoacoustic model. The psychoacoustic model may be of any suitable type.

In some examples, the audio content applied as training input to machine learning model 602 includes noise. In these examples, a noiseless version of the audio content (and not the audio content itself) may, in some cases, be input into error generation function 606 for comparison with the synthesized audio content. In this manner, machine learning model 602 may be trained to reduce noise (e.g., distracting sounds).

As shown, system 500 may feed back the error metric into machine learning model 602. Machine learning model 602 may be configured to use the error metric to adjust the machine learning heuristic applied to the audio content. For example, machine learning model 602 may adjust the machine learning heuristic in a manner that results in an adjusted electrical signal being output by machine learning model 602.

The machine learning model training process described in connection with FIG. 6 may continue until the error metric is below a predetermined threshold, thereby indicating that machine learning model 602 has learned how to generate an electrical signal that accurately and effectively represents audio content input into machine learning model 602. The threshold may be set in any suitable manner.

Figure 7:
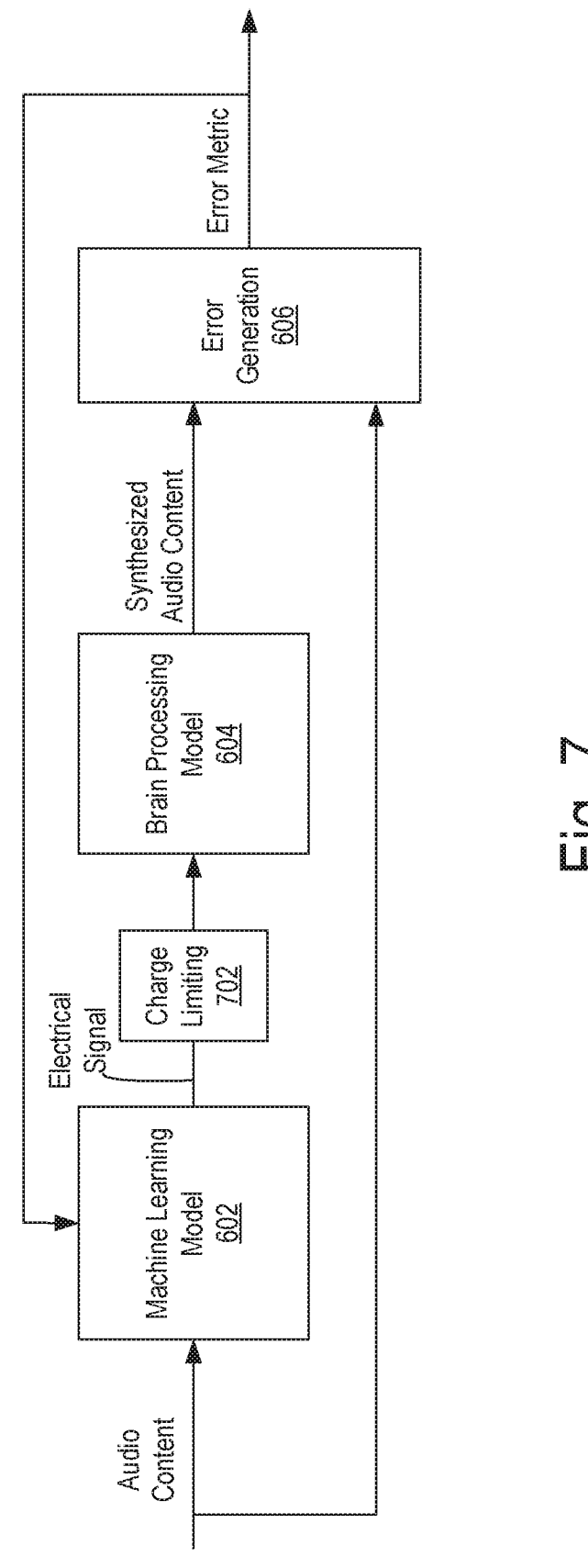
FIG. 7 shows an alternative implementation of the machine learning model training process shown in FIG. 6.

FIG. 7 shows an alternative implementation 700 of the machine learning model training process shown in FIG. 6. Implementation 700 is similar to implementation 600, except that implementation 700 includes a charge limiting function 702. As shown, in implementation 700 the electrical signal output by machine learning model 602 may pass through charge limiting function 702 before being input into brain processing model 604. Charge limiting function 702 is configured to limit an amount of charge of the electrical signal before the electrical signal is applied to brain processing model 604. In this manner, system 500 may ensure that a charge of the electrical signal may stay within medical safety limits.

In some examples, system 500 may train machine learning model 602 in combination with a classifier configured to classify the training audio content as being in a certain environment (e.g., speech in quiet, etc.). In this manner, machine learning model 602 may learn how to adapt to different environments in which a cochlear implant recipient may be located.

The machine learning model training processes described herein may be recipient agnostic. In other words, machine learning model 602 may be trained in a manner that does not take into account specific cochlear implant recipient characteristics and/or hearing profiles. Rather, machine learning model 602 may be trained to output electrical signals that are optimized for cochlear implant recipients in general.

In some alternative implementations, system 500 may train machine learning model 602 to be recipient specific. For example, system 500 may receive data representative of characteristics and/or hearing profiles of a particular recipient and use such data to further train machine learning model 602 to be optimized specifically for the recipient. In some examples, the recipient-specific data may include data representative of an image (e.g., a computerized tomography (CT) scan of the recipient's cochlea) and/or other model data representative of recipient's cochlea and/or other anatomy.

In some examples, system 500 may provide machine learning model 602 with cochlear implant system operating power constraints so that machine learning model 602 may be trained to output a stimulation signal that results in a cochlear implant system staying within the operating power constraints. This may be performed in any suitable manner.

Once machine learning model 602 is trained, system 500 may provide processing unit 108 (and/or any other processing unit included in any cochlear implant system) with access to machine learning model 602. For example, system 500 may transmit data representative of machine learning model 602 to processing unit 108. This may be performed in any suitable manner.

Figure 8:
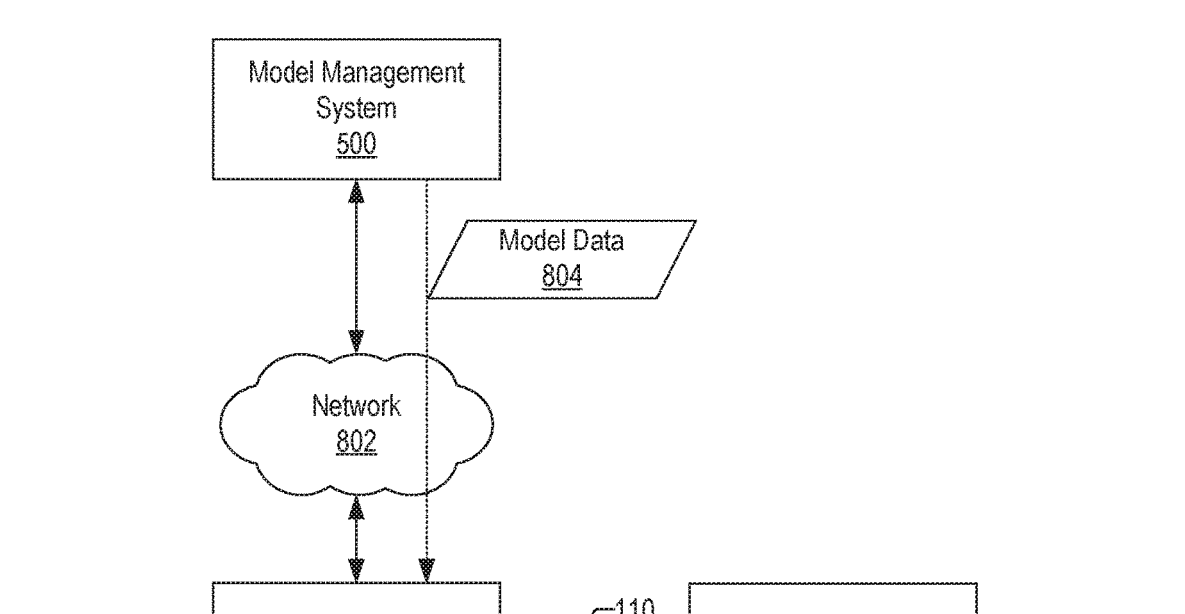
FIG. 8 shows an exemplary configuration in which a network interconnects a model management system and a processing unit of a cochlear implant system.

For example, FIG. 8 shows an exemplary configuration 800 in which a network 802 interconnects system 500 and processing unit 108. Network 802 may include a local area network, a wireless network (e.g., Wi-Fi), a wide area network, the Internet, a cellular data network, and/or any other suitable network. Data may flow between components connected to network 802 using any communication technologies, devices, media, and protocols as may serve a particular implementation.

In configuration 800, system 500 may be configured to transmit model data 804 representative of machine learning model 602 to processing unit by way of network 802. This may be performed in any suitable manner. Processing unit 108 may store model data 804 within a local memory (e.g., memory 112) and thereby access machine learning model 602 to perform one or more processing stages 402, as described herein.

Additionally or alternatively, system 500 may provide processing unit 108 with access to machine learning model 602 by transmitting model data 804 to a computing device (e.g., a fitting device used by a clinician) configured to load model data 804 onto processing unit 108.

Additionally or alternatively, system 500 may provide processing unit 108 with access to machine learning model 602 by providing one or more providing processing unit 108 with one or more application programming interfaces (APIs) that allow processing unit 108 to use machine learning model 602 to process audio content while machine learning model 602 is maintained remotely by system 500. For example, processing unit 108 may use the one or more APIs to transmit data representative of audio content to system 500 by way of network 802. System 500 may apply the data to machine learning model 602 and then transmit data representative of the electrical signal output by machine learning model 602 back to processing unit 108.

Processing unit 108 may be configured to use machine learning model 602 to perform at least one processing stage 402 associated with processing audio content received by processing unit 108. For example, FIGS. 9A-9C show different implementations in which machine learning model 602 is used by processing unit 108 to perform one or more processing stages 402.

Figure 9A:
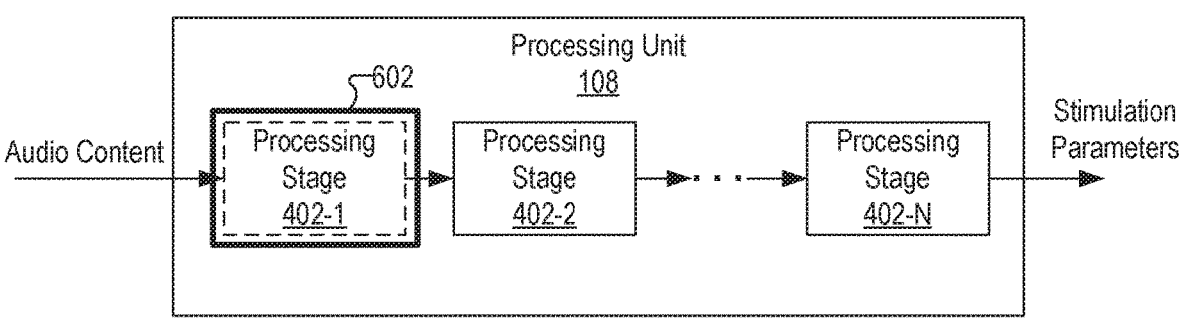
FIGS. 9A-9C show different implementations in which a machine learning model is used by a processing unit to perform one or more processing stages.

In particular, FIG. 9A shows an implementation in which machine learning model 602 is used to perform processing stage 402-1 (e.g., in place of processing components conventionally used to perform processing stage 402-1). In the implementation of FIG. 9A, conventional processing components (e.g., one or more DSPs) may still be used by processing unit 108 to perform one or more other processing stages (e.g., processing stages 402-2 through processing stage 402-N).

As an example of the implementation shown in FIG. 9A, processing unit 108 may be configured to use machine learning model 602 to perform one or more audio content pre-processing operations (e.g., filtering and/or gain correction) on audio content received by processing unit 108. The pre-processed audio content may then be conventionally processed in processing stages 402-2 through processing stage 402-N).

Figure 9B:
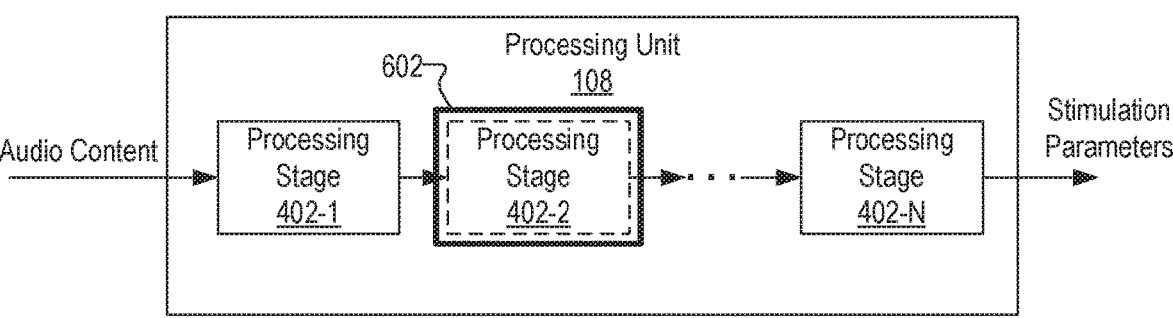
Figure 9C:
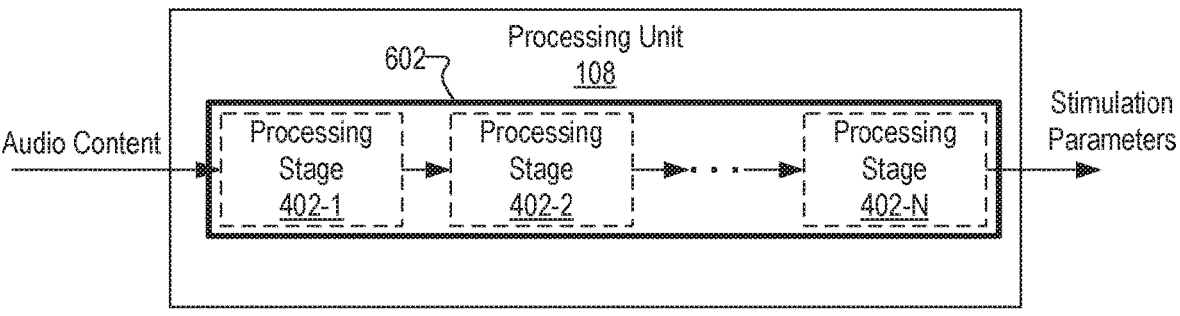

FIG. 9B shows another implementation in which machine learning model 602 is used to perform processing stage 402-2 (e.g., in place of processing components conventionally used to perform processing stage 402-2). In the implementation of FIG. 9B, conventional processing components (e.g., one or more DSPs) may still be used by processing unit 108 to perform one or more other processing stages (e.g., processing stages 402-1 and processing stage 402-N).

As an example of the implementation shown in FIG. 9B, processing unit 108 may use processing stage 402-1 to perform one or more pre-processing operations on audio content received by processing unit 108. Processing unit 108 may then apply the pre-processed audio content to machine learning model 602. In alternative implementations the audio content is not pre-processed prior to being applied to machine learning model 602. In either case, processing unit 108 may use the machine learning model to generate recipient-agnostic parameter data. The recipient-agnostic parameter data include any parameter data that is not specifically configured for use with a recipient. For example, the recipient-agnostic parameter data may include data representative of a noise-reduced version of the audio content, a selection of N of M stimulation channels for use by cochlear implant 102 to represent the audio content to the recipient, and/or any other operation not specific to a recipient.

Continuing with this example, processing unit 108 may apply the recipient-agnostic parameter data to an electrode mapping stage configured to determine, based on the recipient-agnostic parameter data and settings specific to the recipient, recipient-specific stimulation parameters for the recipient. Such recipient-specific stimulation parameters for the recipient may include M levels, T levels, current steering parameters, electrode enabling and disabling parameters, and/or any suitable recipient-specific parameter as may serve a particular implementation. These recipient-specific stimulation parameters may constitute the one or more stimulation parameters that are transmitted to cochlear implant 102.

FIG. 9C shows another implementation in which machine learning model 602 is used to perform all of processing stages 402-1 through processing stage 402-N. In this implementation, conventional processing components are not used by processing unit 108 to perform any of the processing stages 402. Rather, machine learning model 602 is used end-to-end to generate one or more stimulation parameters that are transmitted to cochlear implant 102.

As an example of the implementation shown in FIG. 9C, processing unit 108 may be configured to apply audio content to machine learning model 602 and use machine learning model 602 to generate recipient-specific stimulation parameters that constitute the one or more stimulation parameters that are transmitted to cochlear implant 102. To this end, machine learning model 602 may be configured to perform any of the audio content processing operations described herein.

As another example of any of the implementations shown in FIGS. 9A-9C, processing unit 108 may use machine learning model 602 to determine N of M stimulation channels to be used by cochlear implant 102 to represent audio content to the recipient. In this example, machine learning model 602 may take various factors into account, including energy content within each channel, noise, reverberation, recipient-specific characteristics, and/or other contextual cues as may serve a particular implementation.

Figure 10:
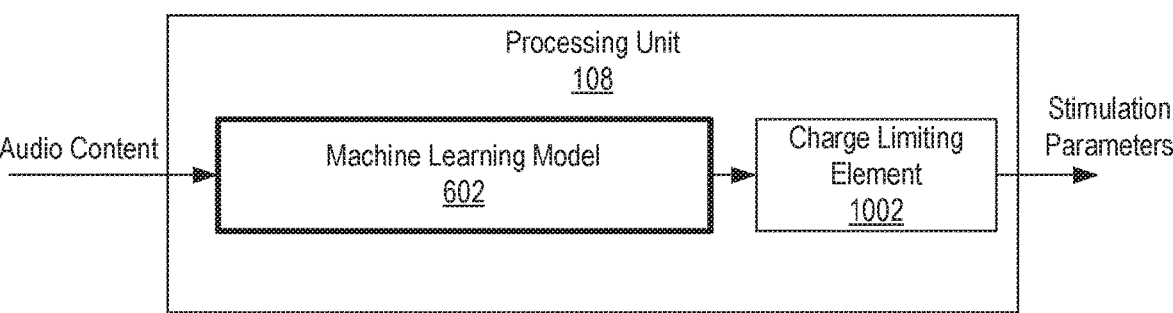
FIG. 10 illustrates an exemplary configuration in which a processing unit is configured to implement a charge limiting element.

FIG. 10 illustrates an exemplary configuration in which processing unit 108 is configured to implement a charge limiting element 1002. Charge limiting element 1002 is configured to prevent stimulation parameters generated using machine learning model 602 from causing the electrical stimulation applied by cochlear implant 102 to have an amount of charge above a threshold (e.g., a medical safety limit). Charge limiting element 1002 may be implemented using any suitable combination of circuitry and processing elements, and may limit charge in any suitable manner.

Figure 11:
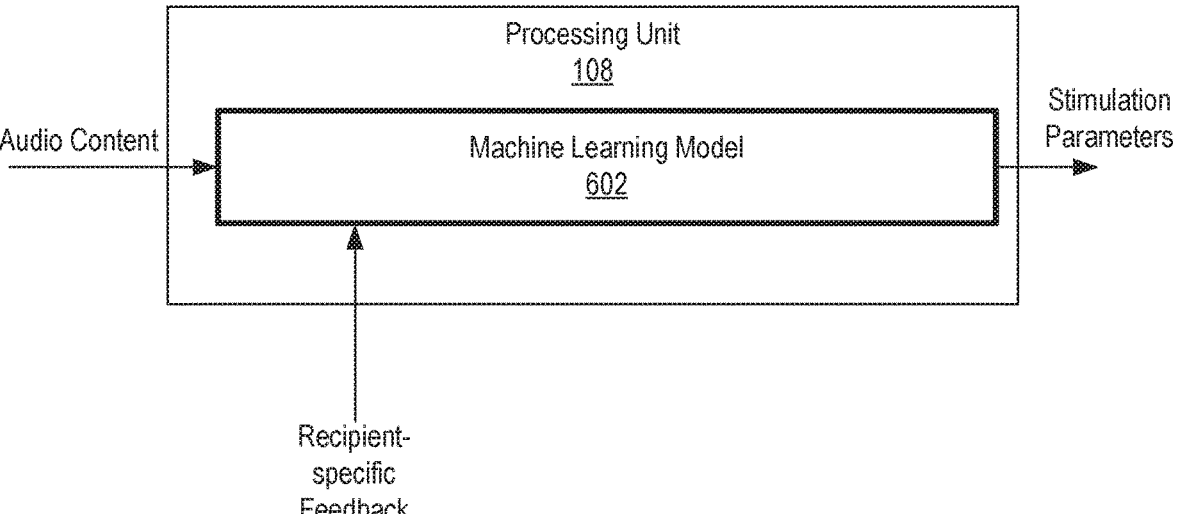
FIG. 11 illustrates an exemplary configuration in which a processing unit is configured to further train a machine learning model based on recipient-specific feedback.

FIG. 11 illustrates an exemplary configuration in which processing unit 108 is configured to further train machine learning model 602 based on recipient-specific feedback. The recipient-specific feedback may be provided by the recipient and/or another user, and may be indicative of an effectiveness of the electrical stimulation applied by cochlear implant 102. The recipient-specific feedback may be subjective (e.g., in the form of verbal responses to questions regarding the effectiveness of the electrical stimulation). Additionally or alternatively, the recipient-specific feedback may be objective. For example, the recipient-specific feedback may be in the form of an evoked response that occurs in response to electrical and/or acoustic stimulation. For example, the evoked response may include an electrocochleographic (ECoG) potential (e.g., a cochlear microphonic potential, an action potential, a summating potential, etc.), an auditory nerve response, a brainstem response, a compound action potential, a stapedius reflex, and/or any other type of neural or physiological response that may occur within a recipient in response to application of electrical and/or acoustic stimulation to the recipient. Evoked responses may originate from neural tissues, hair cell to neural synapses, inner or outer hair cells, or other sources.

Additionally or alternatively, system 500 may train machine learning model 602 based on recipient-specific feedback. For example, processing unit 108 and/or any other computing device may transmit data representative of the recipient-specific feedback to system 500. System 500 may then apply the recipient-specific feedback to machine learning model 602 as training input.

Figure 12:
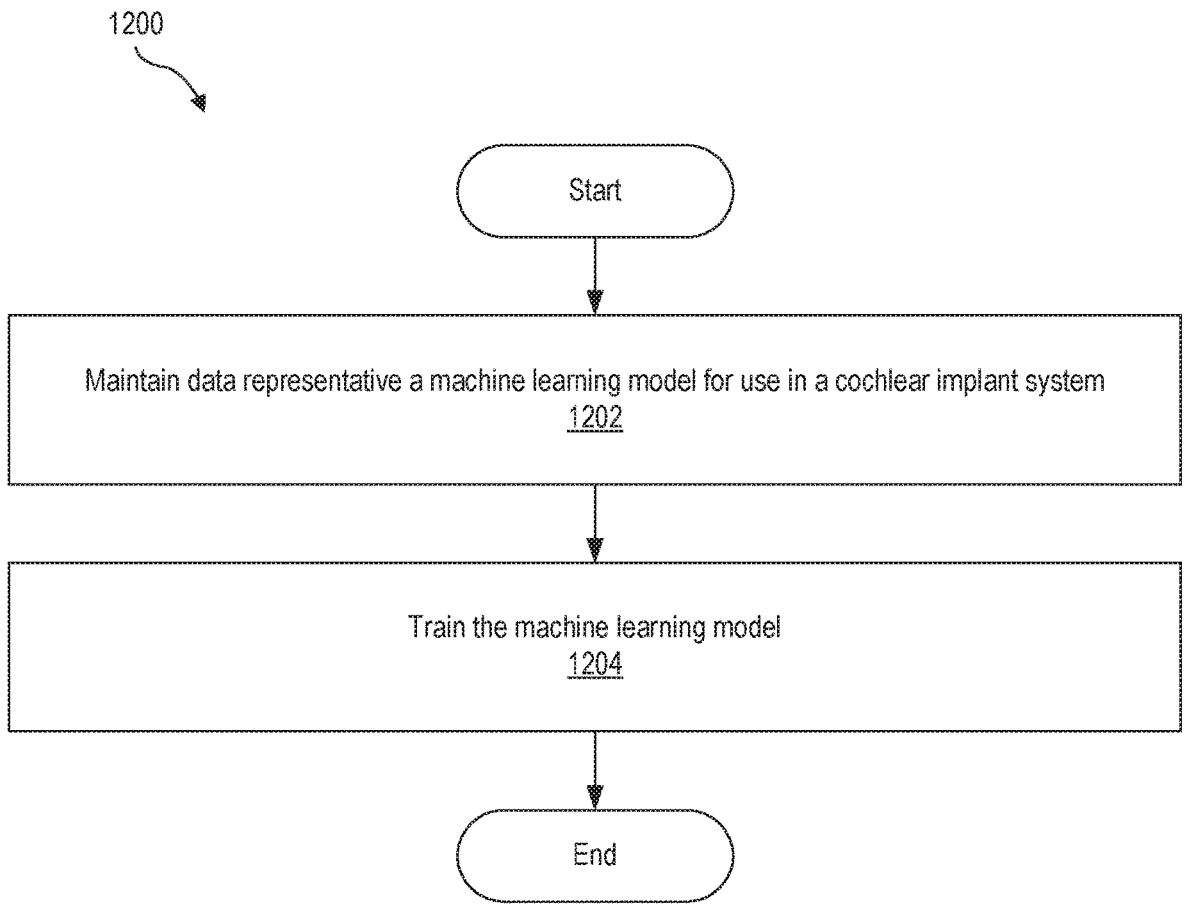

FIG. 12 illustrates an exemplary method 1200 that may be performed by a model management system (e.g., system 500 or any implementation thereof, such as at least one computing device). While FIG. 12 illustrates exemplary operations according to one embodiment, other embodiments may omit, add to, reorder, and/or modify any of the operations shown in FIG. 12. Each of the operations shown in FIG. 12 may be performed in any of the ways described herein.

At operation 1202, a model management system maintains data representative a machine learning model for use in a cochlear implant system.

At operation 1204, the model management system trains the machine learning model.

FIG. 13 illustrates exemplary method 1300 that shows operations that may be performed to train the machine learning model at operation 1204. Each of the operations shown in FIG. 13 may be performed in any of the ways described herein.

At operation 1302, the model management system applies audio content as a training input to the machine learning model, the machine learning model configured to apply a machine learning heuristic to the audio content to output an electrical signal representative of the audio content.

At operation 1304, the model management system applies the electrical signal to a brain processing model, the brain processing model configured to output synthesized audio content representative of the electrical signal.

At operation 1306, the model management system generates an error metric representative of a difference between the audio content and the synthesized audio content.

At operation 1308, the model management system feeds back the error metric into the machine learning model, the machine learning model configured to use the error metric to adjust the machine learning heuristic applied to the audio content.

FIG. 14 illustrates an exemplary method 1400 that may be performed by a processing unit communicatively coupled to a cochlear implant. While FIG. 14 illustrates exemplary operations according to one embodiment, other embodiments may omit, add to, reorder, and/or modify any of the operations shown in FIG. 14. Each of the operations shown in FIG. 14 may be performed in any of the ways described herein.

At operation 1402, a processing unit receives audio content.

At operation 1404, the processing unit accesses data representative of a machine learning model.

At operation 1406, the processing unit uses the machine learning model to perform at least one processing stage associated with processing the audio content to generate one or more stimulation parameters representative of the audio content.

At operation 1408, the processing unit transmits the one or more stimulation parameters to a cochlear implant.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 15:
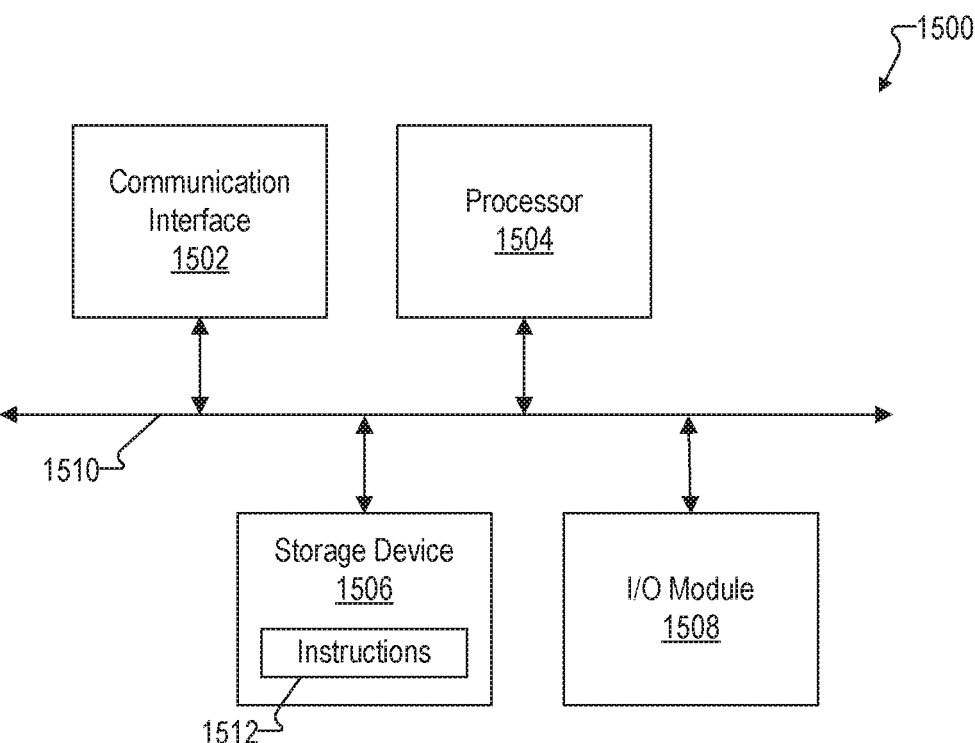
FIG. 15 illustrates an exemplary computing device.

FIG. 15 illustrates an exemplary computing device 1500 that may be specifically configured to perform one or more of the processes described herein. To that end, any of the systems, processing units, and/or devices described herein may be implemented by computing device 1500.

As shown in FIG. 15, computing device 1500 may include a communication interface 1502, a processor 1504, a storage device 1506, and an input/output ("I/O") module 1508 communicatively connected one to another via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data and/or interpreting, executing, and/or directing execution of one or more of the instructions, processes, and/or operations described herein. Processor 1504 may perform operations by executing computer-executable instructions 1512 (e.g., an application, software, code, and/or other executable data instance) stored in storage device 1506.

Storage device 1506 may include one or more data storage media, devices, or configurations and may employ any type, form, and combination of data storage media and/or device. For example, storage device 1506 may include, but is not limited to, any combination of the non-volatile media and/or volatile media described herein. Electronic data, including data described herein, may be temporarily and/or permanently stored in storage device 1506. For example, data representative of computer-executable instructions 1512 configured to direct processor 1504 to perform any of the operations described herein may be stored within storage device 1506. In some examples, data may be arranged in one or more databases residing within storage device 1506.

I/O module 1508 may include one or more I/O modules configured to receive user input and provide user output. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a computing device configured to:
  maintain data representative a machine learning model for use in a cochlear implant system; and
  train the machine learning model by
    applying audio content as a training input to the machine learning model, the machine learning model configured to apply a machine learning heuristic to the audio content to output an electrical signal representative of the audio content, the electrical signal comprising one or more electrical stimulation pulses configured to represent the audio content;
    applying the electrical signal to a brain processing model, the brain processing model configured to output synthesized audio content representative of the electrical signal;
    generating an error metric representative of a difference between the audio content and the synthesized audio content; and
    feeding back the error metric into the machine learning model, the machine learning model configured to use the error metric to adjust the machine learning heuristic applied to the audio content;
a sound processor remote from the computing device; and
a cochlear implant configured to be implanted within a recipient and communicatively coupled to the sound processor by way of a wireless communication link;
wherein the sound processor is configured to:
  receive an audio signal,
  use the machine learning model to perform at least one processing stage with respect to the audio signal to generate one or more stimulation parameters, and
  transmit the one or more stimulation parameters to the cochlear implant by way of the wireless communication link; and
wherein the cochlear implant is configured to:
  receive the one or more stimulation parameters by way of the wireless communication link, and
  apply, based on the one or more stimulation parameters, electrical stimulation representative of the audio signal to the recipient.

2. The system of claim 1, wherein the training continues until the error metric is below a predetermined threshold.

3. The system of claim 1, wherein the processor is further configured to pre-process the audio content before the audio content is applied as the training input to the machine learning model.

4. The system of claim 1, wherein the machine learning model is implemented by a multi-layer neural network.

5. The system of claim 1, wherein the brain processing model is implemented by a vocoder.

6. The system of claim 1, wherein the training of the machine learning model further comprises limiting an amount of charge of the electrical signal before the electrical signal is applied to the brain processing model.

7. The system of claim 1, wherein the computing device is further configured to transmit the data representative of the machine learning model to the sound processor.

8. The system of claim 7, wherein the transmitting comprises transmitting the data representative of the machine learning model to the sound processor by way of a network that interconnects the system and the sound processor.

9. The system of claim 7, wherein the transmitting comprises transmitting the data representative of the machine learning model to a computing device configured to load the data representative of the machine learning model onto the sound processor.

\* \* \* \* \*